(12) United States Patent
Weiss

(10) Patent No.: US 6,428,491 B1
(45) Date of Patent: Aug. 6, 2002

(54) DELIVERY OF ULTRASOUND TO PERCUTANEOUS AND INTRABODY DEVICES

(76) Inventor: Dan Weiss, P.O. Box 283, Hadera (IL), 38102

( * ) Notice: Subject to any disclaimer, the term of this patent is extended or adjusted under 35 U.S.C. 154(b) by 0 days.

(21) Appl. No.: 09/471,364

(22) Filed: Dec. 23, 1999

(30) Foreign Application Priority Data

Aug. 27, 1999 (IL) .................................................. 131623

(51) Int. Cl.$^7$ ............................................. A61M 25/00
(52) U.S. Cl. .............................................. 601/2; 604/22
(58) Field of Search ..................... 601/2–4; 604/264, 604/266, 267, 268, 269, 19, 22

(56) References Cited

U.S. PATENT DOCUMENTS

| | | | |
|---|---|---|---|
| 4,657,536 A | * 4/1987 | Dorman | 604/247 |
| 4,698,058 A | * 10/1987 | Greenfeld et al. | 604/266 |
| 4,836,211 A | * 6/1989 | Sekino et al. | 128/662.05 |
| 4,906,238 A | * 3/1990 | Greenfield et al. | 604/266 |
| 5,329,927 A | * 7/1994 | Gardineer et al. | 128/660.03 |
| 5,725,494 A | 3/1998 | Brisken | |
| 5,728,062 A | * 3/1998 | Brisken | 604/22 |
| 5,735,811 A | * 4/1998 | Brisken | 604/22 |
| 5,904,659 A | 5/1999 | Duarte et al. | |

FOREIGN PATENT DOCUMENTS

| | | |
|---|---|---|
| WO | WO 96/03223 | 2/1996 |
| WO | WO 97/44089 | 11/1997 |
| WO | WO 98/18391 | 5/1998 |
| WO | WO 98/47568 | 10/1998 |

OTHER PUBLICATIONS

Veenstra et al, "Efficacy of A–Impregnated Central Venous Catheters in Preventing Catheter–Related Bloodstream Infection", Journal of AMA, vol. 281, 1999, pp. 261–267.
Qian et al, "The Effect of Ultrasonic Frequency Upon Enhanced Killing of *P. aeruginosa* Biofilms", Annals of Biomedical Engineering, vol. 25, 1997, pp. 69–76.
Pitt et al, "Ultrasonic Enhancement of Antibiotic Action on Gram–Negative Bacteria", Antimicrobial Agents and Chemotherapy, vol. 38, 1994, pp. 2577–2582.

* cited by examiner

*Primary Examiner*—Marvin M. Lateef
*Assistant Examiner*—Eleni Mantis Mercader
(74) *Attorney, Agent, or Firm*—Nixon & Vanderhye P.C.

(57) ABSTRACT

A method and apparatus for reducing morbidity associated with a medical device inserted into the body of a patient. Ultrasonic energy is applied to the device with sufficient intensity to inhibit accretion of biological matter associated with the device while the device is in the body. Typically, the energy is applied to the device in the absence of clinically-observable accretion of biological matter on the device so as to prevent such accretion.

33 Claims, 9 Drawing Sheets

DELIVERY OF ULTRASOUND TO PERCUTANEOUS AND INTRABODY DEVICES

FIELD OF THE INVENTION

The present invention relates generally to invasive medical devices, and specifically to methods and devices for prevention and treatment of infections and thrombosis associated with the use of percutaneous, intravascular and intraluminal devices.

BACKGROUND OF THE INVENTION

Invasive devices such as catheters, central venous catheters, drug delivery tubing, porta-caths, etc., which are passed through body orifices or through an opening made in the patient's skin, are commonplace in medicine today. Such devices are referred to variously as "percutaneous," "intravascular" or "intraluminal" devices. Inherent in their use is the risk of systemic infection secondary to the growth of bacteria in their vicinity, due to the introduction of bacteria with their insertion or bacterial colonization in vivo, and the fluid stasis that can occur with blockage and thus serve as nidus for infection.

Despite innovations such as the local application of antibiotics, infection continues to occur. The organisms involved in these infections are more resistant to antibiotic treatment, presumably due to a change of their membrane permeability when adherent to a catheter surface, or possibly due to other causes. Life-threatening systemic infections can occur as a result. Therefore, medical staff need to regularly remove these invasive devices, disinfect the area, and re-insert a new device. This leads to further concomitant risk of infection, as well as being unpleasant, expensive, and vexing to both staff and patient. A device that would markedly decrease or totally eliminate the need for repetitive catheter replacement, could prove extremely beneficial and allow for a significant decrease in the associated morbidity as noted heretofore.

The accepted means of preventing or treating bacterial contamination is through the use of antibiotics. At the same time, it is widely recognized that the bacteria sequestered in a biofilm that forms on a medical implant are much more resistant to antibiotics than their planktonic counterparts. There have been reports that impregnation of catheters with antiseptics or antibiotics may be helpful in reducing bacterial colonization on the catheter and related bloodstream infection. A recent report to this effect was presented by Veenstra et al., in "Efficacy of Antiseptic-Impregnated Central Venous Catheters in Preventing Catheter-Related Bloodstream Infection," published in the *Journal of the American Medical Association*, Vol. 281 (1999), pp. 261–267, which is incorporated herein by reference.

Studies have shown that the addition of low-frequency ultrasound simultaneous to the application of antibiotics enhances the effectiveness of the antibiotic in killing the bacteria. In vitro experiments to this effect were reported by Qian et al. in an article entitled, "The Effect of Ultrasonic Frequency upon Enhanced Killing of P. aeruginosa Biofilms," published in the *Annals of Biomedical Engineering*, Vol. 25 (1997), pp. 69–76, which is incorporated herein by reference. The authors found that when ultrasonic energy was applied to bacteria sequestered in a biofilm in conjunction with administration of an antibiotic (gentamicin), a significantly greater fraction of the bacteria were killed than by the antibiotic alone. Ultrasound by itself was not found to have any significant effect on the bacteria.

Similarly, Pitt et al. reported in an earlier article entitled "Ultrasonic Enhancement of Antibiotic Action on Gram-Negative Bacteria," in *Antimicrobial Agents and Chemotherapy* Vol. 38 (1994), pp. 2577–2582, which is incorporated herein by reference, that a synergistic effect was observed when ultrasound was applied in combination with gentamicin to in vitro bacterial biofilms. The authors suggest that these results may have application in the treatment of bacterial biofilm infections on implant devices. Ultrasound by itself was not found to be effective in inhibiting bacterial growth, except possibly at power levels high enough to cause cavitation (which would therefore damage surrounding tissues in the body, as well).

There have been a number of reports on the use of ultrasound in the treatment of wounds in vivo. For example, Yudin et al., in "A Comparative Description of Effectiveness of Middling and Low Frequency Ultrasound in Treatment of Festering Wounds," published in *Vestnik Khirurgii* (1995), pp. 63–64, report that ultrasound can have a bactericidal effect in treating wound infection. Similar results were reported by Ukhov et al., in "Indices of Immunity in Treating the Infected Wounds by Low-Frequency Ultrasound," published in *Klin. Khir.* (1990), pp. 10–12. Komrakov et al., in "The Use of Ultrasound and Antibiotics for the Treatment of the Wounds in Patients with a High Risk of Vascular Graft Infection," in *Klin. Khir.* (1990), pp. 10–11, report that low-frequency ultrasound in combination with gentamicin was effective in reducing the level of bacterial wound colonization following vascular graft. All of these articles are incorporated herein by reference.

Clinical ultrasound systems are mainly used for imaging, although there are also some therapeutic devices in use and others that have been suggested in the patent literature. For example, Talish, in PCT patent application PCT/US98/07531, whose disclosure is incorporated herein by reference, describes apparatus for ultrasonic bone treatment. The apparatus includes a therapeutic ultrasonic composite comprising a transducer and an integrated circuit unit positioned adjacent thereto. In operation, the apparatus is placed against the skin adjacent to a wound area, and driving signals are transmitted to the transducer for the creation of therapeutic ultrasound in the area of the bone. Another device of this type, for promotion of vascularization and epitheliazation of a wound inside the body, is described by Duarte et al., in U.S. Pat. No. 5,904,659, whose disclosure is also incorporated herein by reference.

A number of ultrasound devices for percutaneous and intrabody medical use have also been suggested. For example, PCT patent application PCT/IL97/00159, to Ben Haim et al., describes a self-aligning catheter, which uses ultrasound transducers inside the catheter to guide insertion of the probe through physiological tissues.

Tachibana et al., in PCT patent application PCT/US97/19993, whose disclosure is incorporated herein by reference, propose an intraluminal wall drug delivery device. A catheter, which is inserted into a blood vessel for this purpose, comprises at least one puncturing element that is laterally extendable to the catheter's longitudinal axis at its distal end, an ultrasound emitter, and an introducer element that introduces medication into an injection site that is in or beyond the vessel wall. The introducer element delivers a drug for treating local stenosis in the vessel, while the ultrasound emitter generates ultrasound in order to improve the distribution of the drug in the area of the stenosis.

U.S. Pat. No. 5,725,494, to Brisken, whose disclosure is incorporated herein by reference, describes an ultrasonic catheter with a resonantly-vibrating assembly at its distal end for treating vascular clot and plaque. The distal end is positioned in the area of a clot or stenosis in a blood vessel, and the vibrating assembly administers ultrasonic energy to break up the clot or other stenotic lesions. The catheter may also be used in conjunction with a therapeutic agent.

SUMMARY OF THE INVENTION

It is an object of some aspects of the present invention to provide methods and devices for reducing the risks of infection and thrombosis associated with the use of invasive medical devices, and particularly for reducing risks of infection and thrombosis within a lumen into which the invasive device is inserted and in a vicinity of the lumen.

It is another object of some aspects of the present invention to provide methods and devices for treating infection, thrombosis or clotting associated with such invasive devices.

It is a further object of some aspects of the present invention to provide methods and devices for reducing the risks of infection associated with implanted or indwelling devices, such as vascular stents and Goretex vascular anastomoses, and with subcutaneous catheters, such as those used with insulin pumps.

A further object of some aspects of the present invention is to provide devices and methods for delivering ultrasonic energy to invasive devices that achieve good and more or less uniform coverage of the outer surfaces of the device.

Another object of some aspects of the present invention is to provide for a safe, disposable ultrasonic device that can be used intermittently on a patient and then discarded.

In preferred embodiments of the present invention, an ultrasonic transducer is coupled to a device that is inserted into the body of a patient, typically a percutaneous, intravascular and/or other intraluminal device, such as a catheter. While the device is inserted into a patient's body, typically into a blood vessel, the transducer is actuated intermittently to apply ultrasonic energy to the device. Application of the energy, which is optionally accompanied by administration of therapeutic substances, such as antibiotics, anticoagulants and/or fibrinolytic agents, inhibits infection and thrombosis associated with the device. The effect of the ultrasonic energy can be both prophylactic, helping to prevent the occurrence of infection or clotting, and therapeutic, helping to treat the infection or clot if one does occur.

Preferred embodiments of the present invention thus reduce the morbidity associated with the use of invasive devices and enable such devices to be left in place in the body for longer periods than would normally be possible with invasive devices known in the art. Although the efficacy of ultrasound for treating infections and thromboses and in promoting wound healing is known in the art, as exemplified by the publications cited in the Background of the Invention, there has been no suggestion that ultrasound be used prophylactically in conjunction with an invasive device.

In some preferred embodiments of the present invention, the ultrasonic transducer is an integral part of the invasive device and is inserted into the body with the device. In other preferred embodiments, the transducer is attached to the invasive device externally, typically at a location external to the body after the device has been inserted. In this latter case, the transducer may be detached from the invasive device and reattached intermittently, in accordance with a schedule for administration of the prophylactic ultrasonic treatment. In either case, the transducer is preferably coupled and matched to the invasive device so as to transfer ultrasonic energy to all surfaces of the device that are in contact with body tissues and fluids.

In some preferred embodiments of the present invention, an ultrasonic generator is used to administer the ultrasonic energy, the generator comprising a battery and/or external power supply, and an integrated circuit module (ICM), which comprises a signal generator and an interface to the transducer, which is preferably a piezoelectric transducer. Preferably, the transducer is designed to provide directional amplification, or is equipped with a directional horn or other implement for facilitating delivery of the energy to the invasive device. Alternatively, the transducer may be designed as a point source or otherwise non-directional ultrasonic radiator.

The ICM preferably has electric impedance that matches, or is close to, that of the transducer. Further preferably, the ICM is programmable or otherwise adjustable so that different frequencies, intensity levels, and/or operating times can be set, depending on clinical needs and indications. The ICM is most preferably self-adjusting, to match the resonant frequency of the transducer, based on a microprocessor and/or other adjustable electrical circuit. The intensity is preferably maintained within two orders of magnitude of 0.1 $W/cm^2$, that being the safe ultrasound radiation intensity for unlimited periods as determined by the American Institute of Ultrasound in Medicine. Additionally or alternatively, the ICM has an activating switch and on/off indicator.

The transducer preferably includes a matching layer, that optimizes acoustic wave energy transfer from the transducer to the adjacent fluids, invasive devices or body organs, respectively.

In one preferred embodiment of the present invention, the ultrasonic generator comprises a small, easily movable structure attached to the outer part of the invasive device via a spring. The transducer is mounted either in parallel to the axis of the catheter or at an angle, so that vibrational energy can be transferred to the catheter in a direction perpendicular to its axis, along its axis, or via a combination of the two.

In another preferred embodiment of the device, the transducer is tubular in shape and is embedded in the catheter tube itself. Another, similar embodiment uses a transducer of a striped shape with one or more elements, rather than tubular as the aforementioned. These shapes allow the ultrasonic energy to be administered close to the surfaces where it is most effective, and allow for the use of a smaller battery and/or longer operating periods. Similarly, the use of directional guides to direct the wave energy into the inserted parts of the invasive device reduces the needed energy supply.

In other preferred embodiments, the transducer and possibly the ICM are built so as to be located between a proximal end of the catheter and a tube coupled to the proximal end that conveys a fluid, such as a therapeutic agent, to the catheter. Preferably, the transducer is fully immersed in the fluid, and the ultrasonic energy is thus transferred by vibrations in the fluid to other parts of the catheter within the patient's body.

In other preferred embodiments of the invention, the ultrasonic energy is applied to implanted devices, such as vascular stents or Goretex vascular anastomoses. Preferably, the ultrasonic transducer is integrated with the implanted device. The ICM and the activation batteries are optionally also integrated with the implanted device, or alternatively, they are external to the body. Further alternatively, the ultrasonic energy is applied from outside the body through an insertion device. As a still further alternative, the transducer is attached to the skin or to a balloon-type fluid container that is firmly attached to the skin. The ultrasound energy is radiated from the transducer, through the fluid in the balloon, to an intravascular tube in a vein or artery or to the implanted device itself that is below the skin.

There is therefore provided, in accordance with a preferred embodiment of the present invention, a method for reducing morbidity associated with a medical device inserted into the body of a patient, including applying ultrasonic energy to the device with sufficient intensity to inhibit accretion of biological matter associated with the device while the device is in the body. Preferably, applying the ultrasonic energy includes applying energy to the device in the absence of clinically-observable accretion of biological matter on the device so as to prevent such accretion.

In some preferred embodiments, applying the ultrasonic energy includes integrating an ultrasonic transducer in the device and actuating the transducer.

In other preferred embodiments, applying the ultrasonic energy includes coupling a source of ultrasonic energy outside the body to the invasive device in the body. Preferably, coupling the source of ultrasonic energy includes fixing a transducer to a portion of the invasive device that is outside the body. Alternatively, coupling the source of ultrasonic energy includes transferring energy to a fluid that passes through the invasive device, wherein transferring the energy to the fluid includes immersing at least a portion of the transducer in the fluid. Further alternatively, coupling the source of ultrasonic energy includes coupling a transducer to the skin of the body adjacent to a location of the invasive device in the body.

Preferably, applying the ultrasonic energy includes applying energy to the device so as to inhibit bacterial growth on the device. Additionally or alternatively, applying the ultrasonic energy includes applying energy to inhibit formation of a clot on the device.

In a preferred embodiment, the method includes administering a therapeutic agent in a vicinity of the device inside the body in conjunction with applying the ultrasonic energy. Preferably, the therapeutic agent includes an antibacterial agent or, alternatively or additionally, an anti-clotting agent. Most preferably, administering the therapeutic agent includes coating at least a portion of the device with the therapeutic agent.

There is also provided, in accordance with a preferred embodiment of the present invention, apparatus for reducing morbidity associated with a device inserted into the body of a patient, including an ultrasonic energy generator, which is coupled to apply ultrasonic energy to the device with sufficient intensity to inhibit accretion of biological matter associated with the device while the device is in the body.

Preferably, the ultrasonic energy generator includes an ultrasonic transducer and an integrated circuit module, which drives the transducer so as to control one or more parameters of the energy applied to the device. Most preferably, the integrated circuit module generates an oscillating electrical current to drive the transducer, and wherein the module adjusts a frequency of the oscillating current so as to match a resonant frequency of the transducer. Optionally, the integrated circuit module is coupled to the transducer by a connector, so that a portion of the apparatus containing the transducer may be disposed of after use or be sterilizable, while another portion including the integrated circuit module is reused.

There is further provided, in accordance with a preferred embodiment of the present invention, an ultrasonic energy generator for use with an invasive device, including:

a generator body, adapted to be mechanically coupled to a proximal portion of the invasive device that is outside the body; and a transducer, held by the generator body so as to apply ultrasonic energy to the invasive device while a distal portion of the device is in the body.

Preferably, the generator body includes a fastener, which is adapted to fix the transducer to the invasive device. Alternatively or additionally, the generator body is shaped so as to be insertable into a lumen of the invasive device.

Further alternatively or additionally, the generator body includes a fluid container, containing a fluid that passes through the invasive device, and the transducer is coupled to transfer ultrasonic energy to the device through the fluid. Preferably, at least a portion of the transducer is immersed in the fluid. Further preferably, the container is shaped so as to concentrate the ultrasonic energy from the transducer into the device.

There is moreover provided, in accordance with a preferred embodiment of the present invention, a medical device, including:

an intrabody member, for insertion into the body of a patient; and an ultrasonic energy generator, which is coupled to apply ultrasonic energy to the intrabody member with sufficient intensity to inhibit accretion of biological matter associated with the device while the device is in the body.

Preferably, the ultrasonic energy is applied in conjunction with administration of a therapeutic agent in a vicinity of the intrabody member inside the body, wherein the therapeutic agent is most preferably adherent to a surface of the intrabody member. Alternatively, the therapeutic agent is injected into the body through the intrabody member or via other means, and is used according to its pharmaco-kinetics.

In a preferred embodiment, the intrabody member includes a catheter. In another preferred embodiment, the intrabody member includes an implanted element, such as a vascular implant. In still another preferred embodiment, the intrabody member includes a short-term transcutaneous insert, wherein most preferably, the device includes a pump, which is coupled to inject a fluid into the body through the insert, and an energy source for driving the ultrasonic generator, which is integrated with the pump.

There is additionally provided, in accordance with a preferred embodiment of the present invention, apparatus for reducing morbidity associated with a device inserted into the body of a patient, including an ultrasonic transducer, which is coupled to the skin of the body adjacent to a location of the device in the body and is adapted to apply ultrasonic energy through the skin to the device with sufficient intensity to inhibit accretion of biological matter associated with the device while the device is in the body.

There is also provided, in accordance with a preferred embodiment of the present invention, a method for reducing morbidity associated with a medical device inserted into the body of a patient, including:

coupling a transducer to an outer surface of the body adjacent to a location of the device in the body; and applying ultrasonic energy to the device through the outer surface of the body with sufficient intensity to inhibit accretion of biological matter associated with the device while the device is in the body.

There is still further provided, in accordance with a preferred embodiment of the present invention, a medical device, including:

a tubular member for insertion into the body of a patient, the member comprising a wall that defines a lumen therethrough; and an ultrasonic energy generator, which is coupled to apply ultrasonic energy to the wall of the tubular member with sufficient intensity to inhibit accretion of biological matter associated with the device while the device is in the body.

Preferably, the ultrasonic energy generator comprises an ultrasonic transducer, which is integrally contained within the wall of the tubular member. Additionally or alternatively, the ultrasonic energy generator is generally tubular, and has a diameter similar to a diameter of the tubular member.

The present invention will be more fully understood from the following detailed description of the preferred embodiments thereof, taken together with the drawings in which:

DETAILED DESCRIPTION OF PREFERRED EMBODIMENTS

Figure 1:
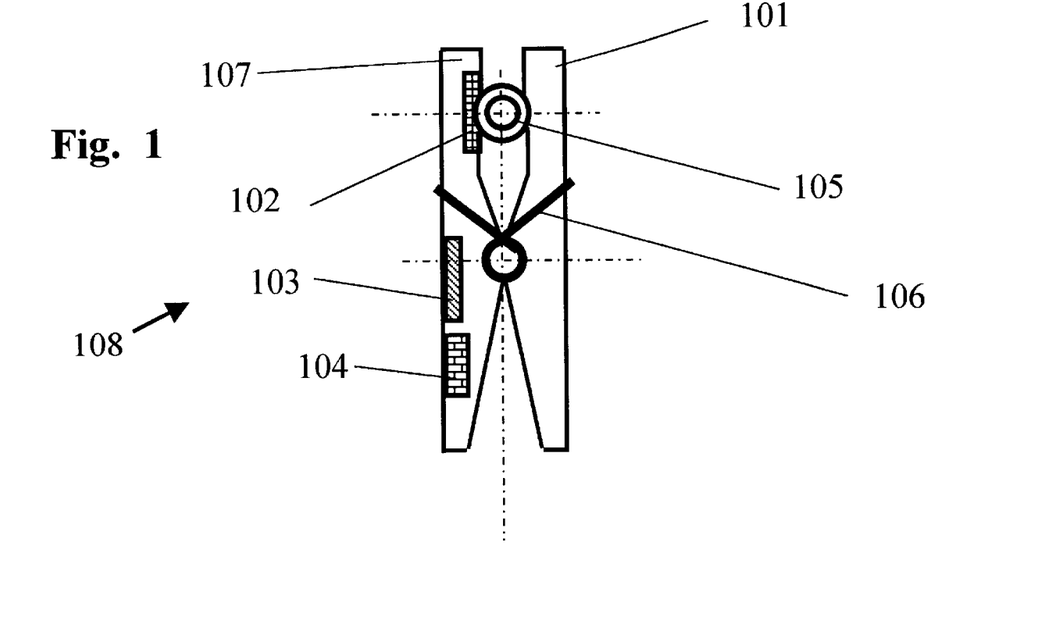
FIG. 1 is a schematic, sectional illustration of an ultrasonic generator attached to the outside of an invasive medial device, in accordance with a preferred embodiment of the invention.

Reference is now made to FIG. 1, which is a schematic, sectional illustration of an invasive medical device 105, coupled to an ultrasonic generator 108, in accordance with a preferred embodiment of the present invention. Device 105 typically comprises a catheter, such as a plasma or blood transfusion catheter, dialysis catheter, infusion catheter, urinary catheter or any other suitable type of device. Generator 108 comprises a small, easily movable structure, which is attached to a part of device 105 outside the patient's body by means of a quick-connect fastener 101. In the present embodiment, a spring 106 secures the generator to the catheter.

Generator 108 comprises a transducer 102, an integrated circuit module (ICM) 103, and a battery 104. The transducer preferably comprises a piezoelectric transducer, made up of one or more layers, but may alternatively comprise a magnetostrictive transducer or any other suitable type of ultrasonic source known in the art. The transducer may be of a bending type, a transverse type, a shear type or any other suitable type known in the art, comprising a single layer or multiple layers. The use of any such ultrasonic source in the manner described in this patent application is considered to be within the scope of the present invention. Furthermore, the transducer preferably includes a matching layer (not shown), as is known in the art, for matching the acoustic impedance of the transducer to the device or medium to which ultrasonic energy is to be transferred. ICM 103 preferably comprises a driver circuit, which draws energy from the battery and drives the transducer at an appropriate frequency, and a microprocessor or logic circuit for controlling operation of the ultrasonic generator. Preferably, generator 108 also comprises an on/off switch and, optionally, other controls, as well as an indicator, such as a LED.

Transducer 102 is preferably mounted parallel to a longitudinal axis of catheter 105, or alternatively, is inclined at an angle relative to the axis. optionally, the transducer comprises multiple segments, which are driven by respective electrodes so as to control and vary the direction of vibrations induced in the transducer, as is known in the art. In this manner, vibrational energy can be transferred to the catheter perpendicular to its axis, along its axis, or in a combination of the two directions. The impedance of the generator is matched to that of the transducer 102 in order to maximize the wave energy transmitted from the transducer to the catheter and minimize losses. Preferably, a reflecting or flexible medium (not shown) is inserted between a body 107 of fastener 101 and transducer 102.

In operation, invasive device 105 is inserted into the body of a patient, typically into a blood vessel, by medical personnel. Fastener 101 is then fixed to a part of device 105 outside the patient's body, and generator 108 is actuated to apply ultrasonic energy to the device. Optionally, an outer surface of device 105 is coated or impregnated with a therapeutic substance, such as an antiseptic, antibiotic or thrombolytic agent. Alternatively, device 105 is operated in conjunction with a therapeutic agent injected into the bloodstream. The ultrasonic energy applied by generator 108, together with or independent of the therapeutic agents, inhibits colonization of bacteria on the surface of the invasive device and in a vicinity thereof within the body. It also tends to inhibit the formation of clots on and around the invasive device. Furthermore, when infection or clotting does occur, generator 108 may be actuated to help treat the condition and eliminate the infection or clot.

As long as invasive device 105 is kept in the patient's body, application of the ultrasonic energy by generator 108 is repeated, either continuously or, more preferably, intermittently. In the latter case, generator 108 is actuated as often as necessary, and at an appropriate frequency and amplitude, in order to ensure that infection and thrombosis are prevented. Fastener 101 may be left in position for as long as device 105 is in the body, or it may be detached and then re-attached as needed. Preferably, ICM 103 is programmable or otherwise adjustable so as to provide the appropriate amount of ultrasonic energy required for prophylactic or therapeutic purposes, without unnecessarily running down battery 104 or heating the tissues around the invasive device. The intensity is preferably maintained within two orders of magnitude of 0.1 W/cm$^2$, that being the safe ultrasound radiation intensity for unlimited periods as determined by the American Institute of Ultrasound in Medicine. The frequency is preferably between 20 and 120 kHz, although other frequency ranges may also be used. The ICM 103 preferably includes an auxiliary connector for an optional, external power supply (not shown).

Figure 2:
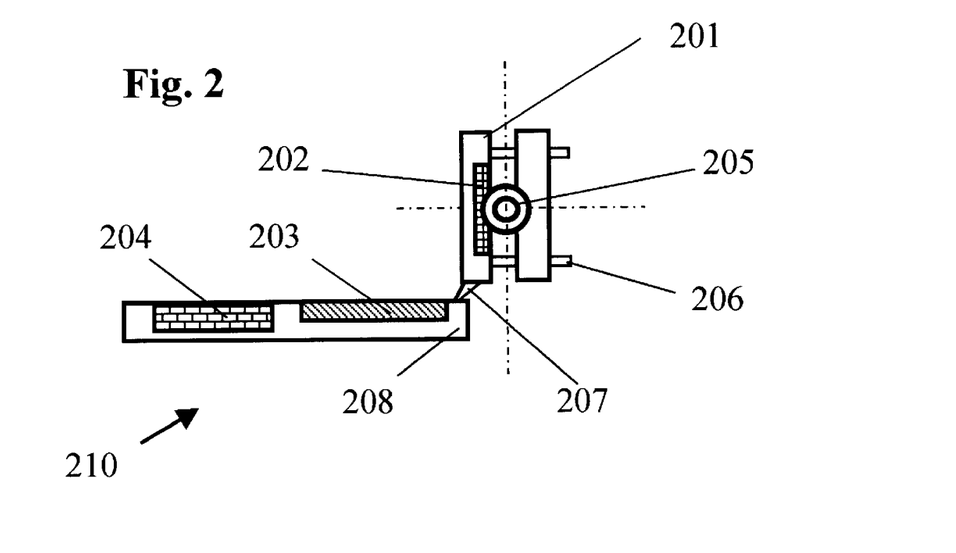
FIG. 2 is a schematic, sectional illustration of a two-part ultrasonic generator attached to an invasive medical device, in accordance with a preferred embodiment of the present invention.

FIG. 2 is a schematic, sectional illustration of an ultrasonic generator 210 coupled to a catheter 205, in accordance with another preferred embodiment of the present invention. A body of generator 210 is divided into two parts, 201 and 208. Part 201 contains a piezoelectric transducer 202, single- or multi-layered, which is fastened to catheter 205 by pins or bolts 206, preferably using wing nuts or other quick release fasteners. Part 208 houses an ICM 203 and a battery 204. The two parts are connected by a flexible joint 207, or alternatively or additionally, by long electrical wires with a suitable connector (not shown) . The joint is designed so as not restrict the vibration of part 201. Operation of generator 210 is as described hereinabove with reference to FIG. 1.

Figure 3:
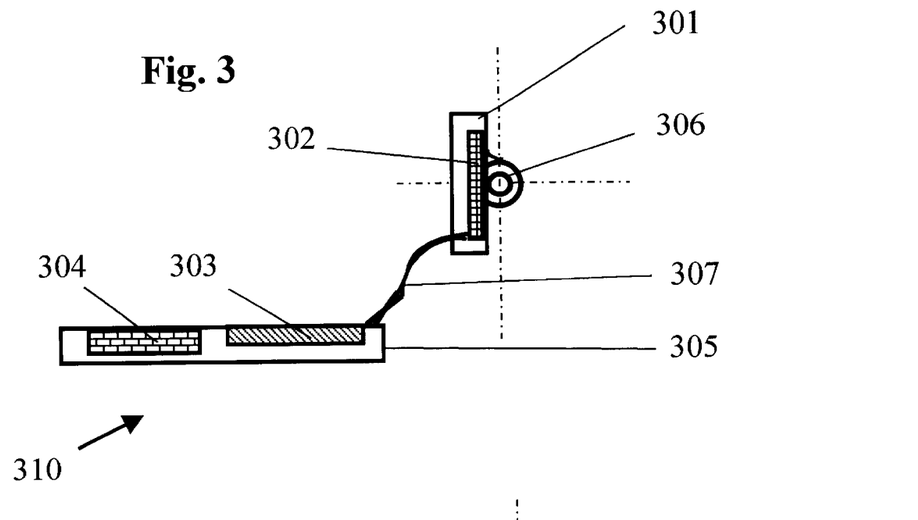
FIG. 3 is a schematic, sectional illustration of an ultrasonic generator integrated with an outer portion of an invasive medical device, in accordance with a preferred embodiment of the present invention.

FIG. 3 is a schematic, sectional illustration of an ultrasonic generator 310 fixed to a catheter 306, in accordance with still another preferred embodiment of the present invention. In this embodiment, a structure 301, which includes a transducer 302, is integrally fixed to or built as a part of an outer section of catheter 306. This in contrast to the preceding embodiments, in which the structure was external to the catheter. An ICM 303 and a battery 304 are contained in another part 305 of generator 310, coupled by a flexible joint 307 or possibly by a quick-connect coupling to structure 301.

Alternatively, battery 304 may be replaced by a miniature power supply (not shown), which runs on lines power. The use of lines power enables generator 310 to be operated for extended periods, without the danger or inconvenience of running down the battery. In this case, structure 301 with transducer 302 is preferably disposed of after use, while part 305 is reused. Instead of joint 307, structure 301 and part 305 may be connected by a suitable cable, with a cable connection. Such a separation of the transducer portion from the power supply and ICM portion of the ultrasonic generator may likewise be implemented, mutatis mutandis, in the other preferred embodiments of the present invention.

Figure 4:
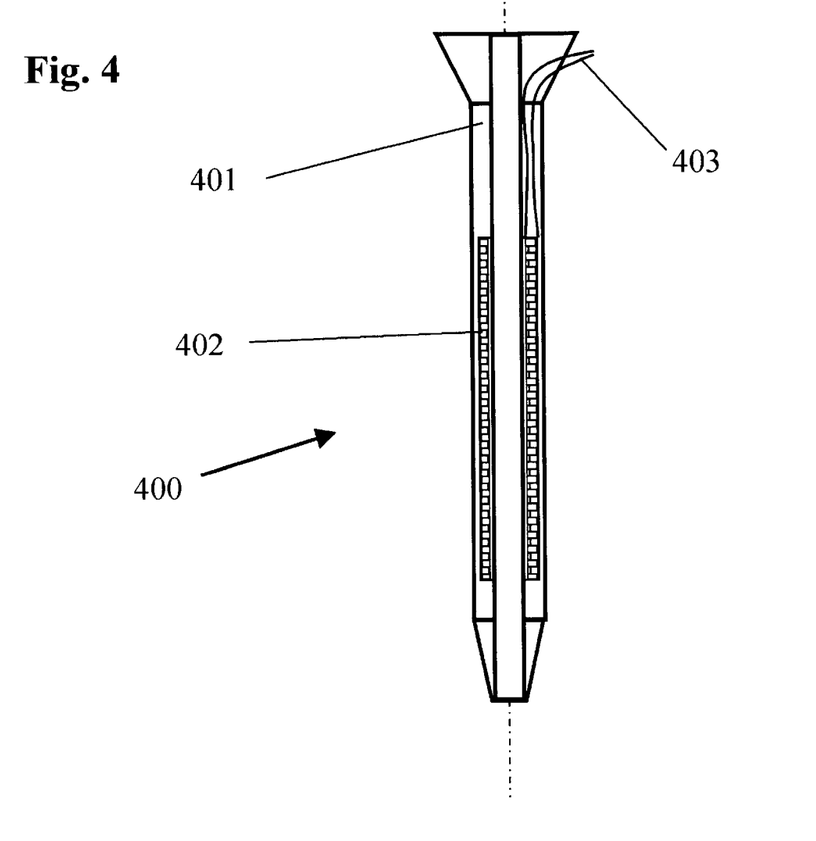
FIG. 4 is a schematic, sectional illustration of a tubular ultrasonic generator embedded in tubing of an invasive medical device, in accordance with a preferred embodiment of the present invention.

FIG. 4 is a schematic, sectional illustration of a catheter 400 that includes an integral ultrasonic transducer 402, in accordance with another preferred embodiment of the invention. Transducer 402 is preferably tubular in shape and is embedded in a wall 401 of the catheter. The transducer is connected by an electrical wire 403 to an ICM and power supply in a separate outer structure (not shown in this figure), such as that described hereinabove with reference to FIG. 2, parts 203, 204 and 208. Integration of transducer 402 in catheter 400 ensures that ultrasonic energy will be distributed efficiently and more or less uniformly to all parts of the catheter. Preferably, the catheter with the transducer is used for a single patient and is then disposed of, while the ICM and power supply are detached and reused. Alternatively, the entire catheter is sterilizable, for example, by gas or by autoclaving, and may be reused multiple times.

Figure 5:
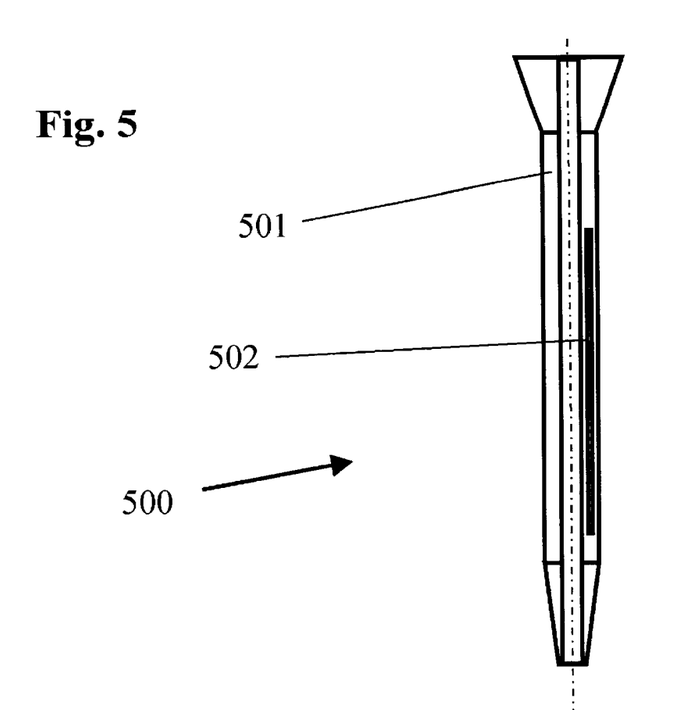
FIG. 5 is a schematic, sectional illustration of an ultrasonic generator embedded in tubing of an invasive medical device, in accordance with another preferred embodiment of the present invention.

FIG. 5 is a schematic, sectional illustration of a catheter 500 in which a transducer 502 is again embedded in a wall 501 of the catheter, in accordance with still another preferred embodiment of the present invention. In this case the transducer comprises one or more elements of a linear shape, rather than being cylindrical or tubular as shown in FIG. 4. Linear transducers of this sort are generally simpler to manufacture and less costly than the cylindrical transducer of FIG. 4.

Although the embodiments of FIGS. 4 and 5 are described with reference to catheters 400 and 500, transducers may be incorporated in like manner into implantable devices, such as stents and vascular anastamoses. In the context of the present patent application and in the claims, such implantable devices, as well as those portions of invasive devices that are inserted into the body temporarily, such as percutaneous, intravascular and other intraluminal devices, are referred to collectively as intrabody members. The ICM and power supply in such cases may also be implanted in the body, typically in proximity to the implantable device itself. Alternatively, a connector may be provided to the implantable device, which connector is accessible from outside the body to provide electrical energy to drive the transducer when needed. Further alternatively, when the implantable device is near the body surface, a needle may be inserted through the skin to contact and provide energy to the implant, or energy may be transferred through the skin, as described hereinbelow with reference to FIG. 9.

Figure 6:
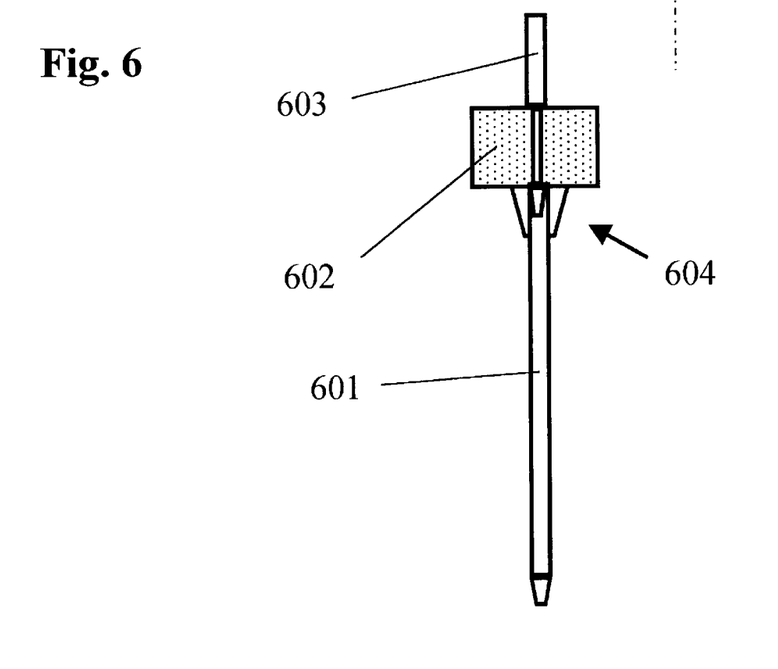
FIG. 6 is a schematic side view of an ultrasonic generator located between a catheter and a tube that conveys medication thereto, in accordance with a preferred embodiment of the present invention.

FIG. 6 is a schematic side view of an ultrasonic generator 602 fixed to a catheter 601, in accordance with yet another preferred embodiment of the present invention. Generator 602 comprises a transducer and ICM, as described hereinabove. The generator is attached to the catheter or other invasive device by means of a friction or positive snap-on mechanism 604. Generator 602 is preferably located between catheter 601 and tubing 603 that is used to convey medication to the catheter. The transducer thus transfers ultrasonic energy both to the catheter itself and to fluid passing through the tubing and into the catheter. This configuration tends to improve the efficiency of energy transfer and also, by imparting energy to the fluid, to increase the therapeutic efficacy of the medication.

Figure 7:
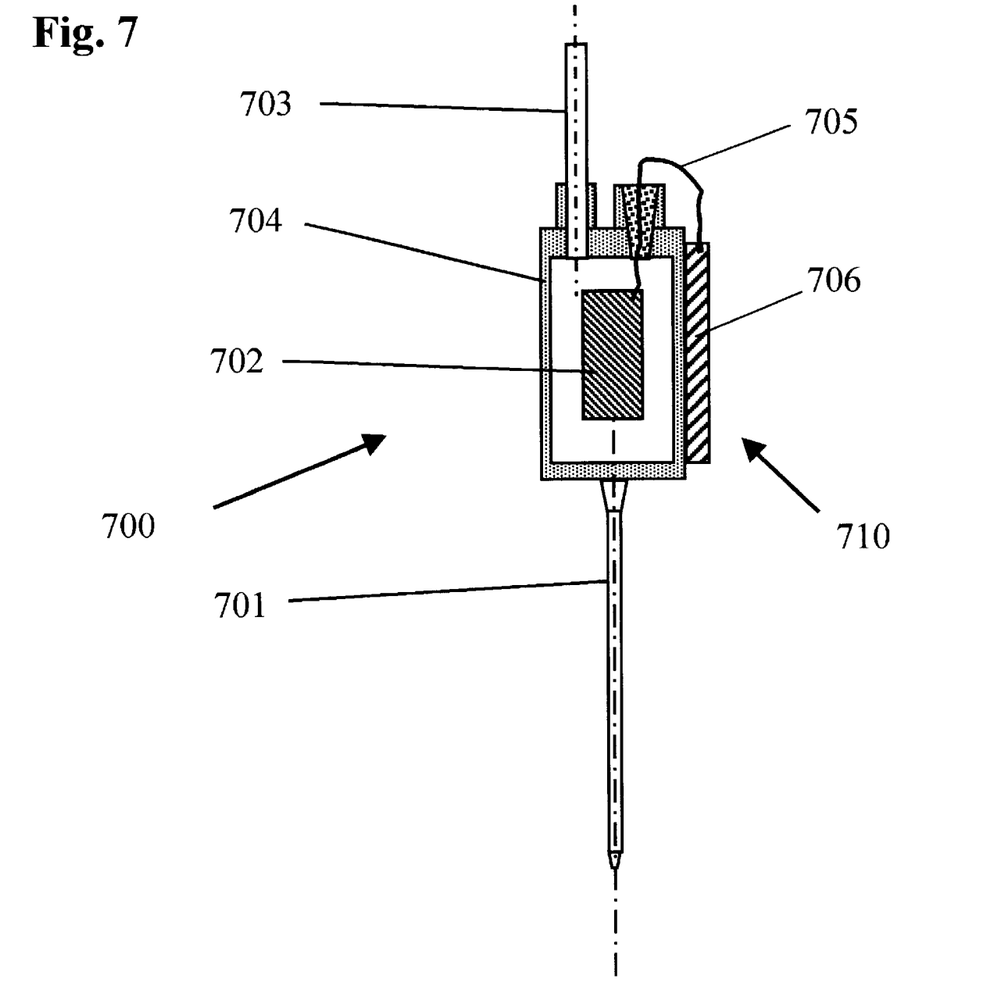
FIG. 7 is a schematic, sectional illustration of a catheter to which an ultrasonic generator is coupled, in accordance with a preferred embodiment of the present invention.

FIG. 7 is a schematic, sectional illustration of a catheter assembly 700, which includes an integral ultrasonic generator 710, in accordance with a preferred embodiment of the present invention. Generator 710 is integrated with a container 704, in which a transducer 702 is immersed. The container is filled with fluid received from tubing 703 outside the body, and connects to tubing 701 entering the body. Tubing 701 is typically a part of a catheter or is associated with a catheter that is inserted into the body.

Transducer 702 is either fixed or free-floating inside container 704 and is connected via leads 705 to the ICM, which is depicted together with its power supply as a control unit 706. In this embodiment, the transducer is fully immersed in the fluids that fill the container, and radiates its ultrasonic vibration through the fluids to tube 701. This vibration is then transferred from tube 701 to the fluids around it in the body, where the ultrasonic energy is most needed for enhancing antibiotic activity, since this is the area that is most prone to bacterial contamination. The transducer may be of a bending type, a transverse type, a shear type or any other suitable type known in the art, comprising a single layer or multiple layers. Most preferably, transducer 702 is a directional transducer, designed to radiate ultrasonic energy preferentially toward tube 701.

Figure 8:
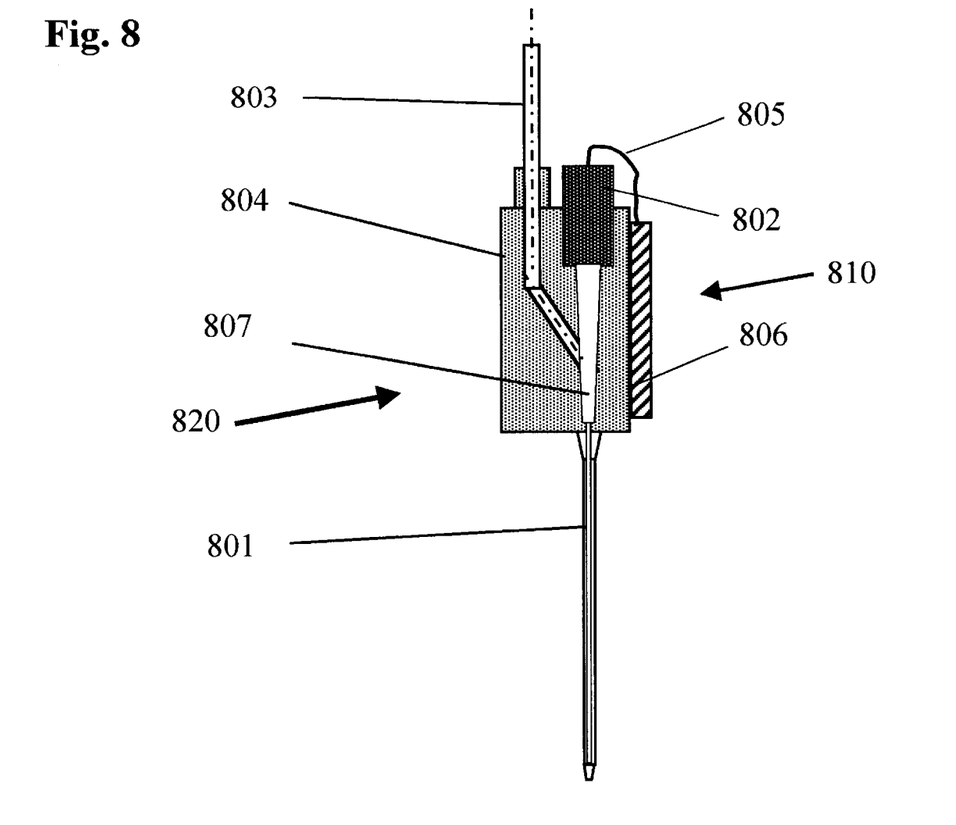
FIG. 8 is a schematic, sectional illustration of a catheter to which an ultrasonic generator is coupled, in accordance with another preferred embodiment of the present invention.

FIG. 8 is a schematic, sectional illustration of a catheter assembly 820, in accordance with a preferred embodiment of the present invention. Assembly 820 is similar to assembly 700 shown in FIG. 7, except that rather than being immersed in fluid in container 704, a transducer 802 in assembly 820, powered by a control unit 806 via leads 805 communicates with the fluid on only one of the transducer faces. The transducer is fixed to a container 804 by a soft, elastic material, which seals the fluid inside but allows the transducer to vibrate. The fluid is fed to the container by tubing 803. The vibrations of the transducer are coupled to the fluid in a tube 801 by a directional horn 807, which focuses the ultrasonic energy into the tube.

Figure 9:
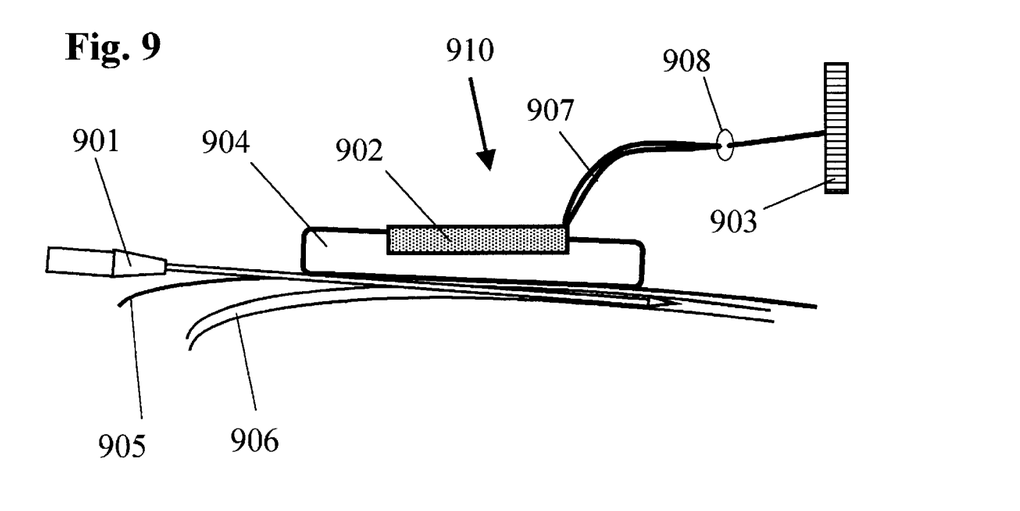
FIG. 9 is a schematic, sectional illustration of an ultrasound generator coupled to a balloon-type fluid container adjacent to an invasive medical device, in accordance with a preferred embodiment of the present invention.

FIG. 9 is a schematic, sectional illustration of an ultrasonic generator 910, which transfers energy through skin 905 of a patient to an invasive device 901 in the patient's body, in accordance with a preferred embodiment of the present invention. In the example shown in this figure, device 901 comprises a catheter inserted into a blood vessel 906. It will be understood, however, that generator 901 may similarly be used to impart energy to other types of invasive devices that are sufficiently near the skin surface to receive the energy. Generator 910 is preferably fixed to the skin by straps, tape, or other means (not shown in the figures).

Generator 910 comprises a transducer 902, which is driven by a control unit 903 via leads 907, possibly coupled by a connector 908. Preferably, the transducer is attached to a balloon-type fluid container 904, which is firmly attached to the skin and facilitates efficient and uniform transfer of ultrasonic energy. The ultrasound wave energy is radiated from the transducer 902, through the fluid in the balloon, to catheter 901, and to vessel 906 below the skin. Alternatively, transducer 902 may be attached directly to the skin, without container 904, preferably by use of an appropriate gel, as is known to the art.

Figure 10:
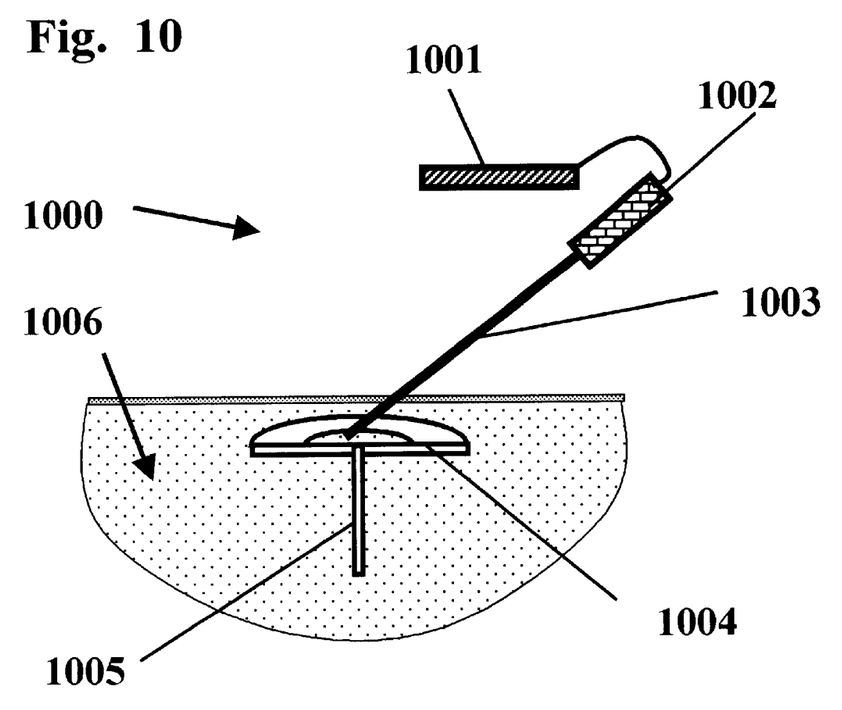
FIG. 10 is a schematic, sectional illustration of an ultrasonic generator coupled to apply ultrasonic energy to a subcutaneous, long-term catheter, in accordance with a preferred embodiment of the present invention.

FIG. 10 is a schematic, sectional illustration of another ultrasonic generator 1000, which is used to induce ultrasonic vibration of a subcutaneous, long-term catheter 1005, in accordance with a preferred embodiment of the present invention. Catheter 1005, commonly known as a "Port-a-Cath," is implanted in subcutaneous tissue 1006, typically for the purpose of long-term intravascular drug delivery from a drug reservoir 1004, as is known in the art. Generator 1000 is preferably coupled to a needle 1003, which is inserted through the patient's skin in order to refill reservoir 1004 with the drug. An ultrasonic unit 1002, comprising a suitable transducer and, preferably, an ICM, as described hereinabove, is driven by a power source 1001 to vibrate the needle. The needle conveys the vibrations to reservoir 1004 and catheter 1005.

Figure 11:
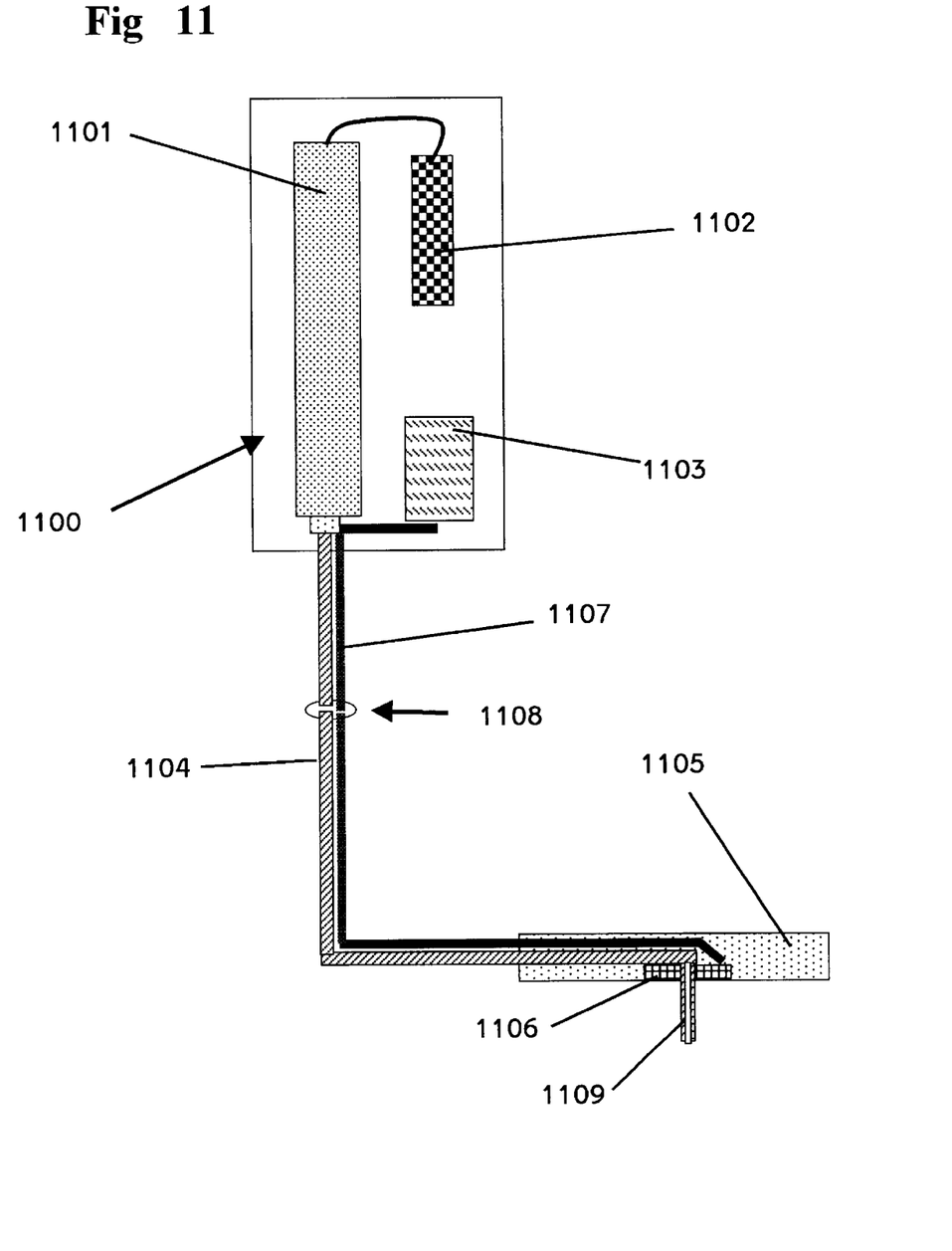
FIG. 11 is a schematic, sectional illustration of a pump for subcutaneous drug delivery, incorporating an ultrasonic generator, in accordance with a preferred embodiment of the present invention.

FIG. 11 is a schematic, sectional illustration showing a pump system 1100 for subcutaneous delivery of a drug, such as insulin, in which an ultrasonic generator is integrated, in accordance with a preferred embodiment of the present invention. System 1100 comprises an electromechanical pump 1101, powered by an energy source 1102, and coupled by tubing 1104 to deliver the drug via a subcutaneous catheter 1109. An ICM 1103 drives an ultrasonic transducer 1106 via a cable 1107, which preferably runs along tubing 1104. The transducer and catheter are together held in place against the patient's skin by an adhesive pad 1105. A connector 1108 is preferably used to attach and detach both tubing 1104 and cable 1107, so that system 1100 can be connected and used when and as needed, without having to attach and remove pad 1105 every time. While system 1100 is connected, the drug is delivered via catheter 1109, and transducer 1106 is used to vibrate the catheter, so that pad 1105 with the catheter can be left in place for extended periods.

Figure 12:
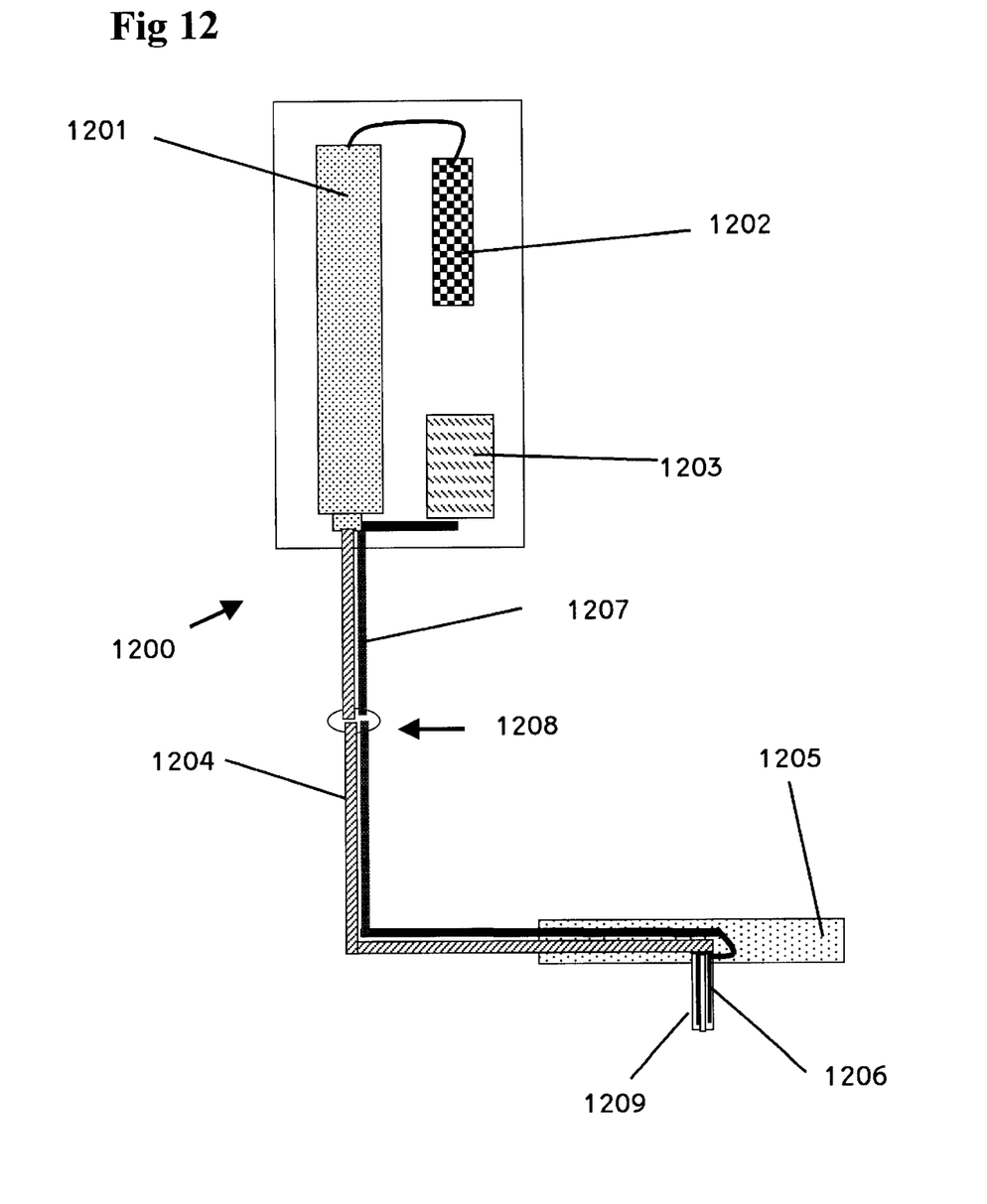
FIG. 12 is a schematic, sectional illustration of a pump for subcutaneous drug delivery, incorporating an ultrasonic generator, in accordance with another preferred embodiment of the present invention.

FIG. 12 is a schematic, sectional illustration of another pump system 1200, in accordance with a preferred embodiment of the present invention. System 1200 is essentially similar to system 1100 shown in FIG. 11, and parts 1201–1209 are respectively substantially identical to parts 1101–1109, described above. In the embodiment of FIG. 12, however, transducer 1206 is tubular and placed inside the tubular part of catheter 1209, rather than against the skin as in FIG. 11.

Figure 13:
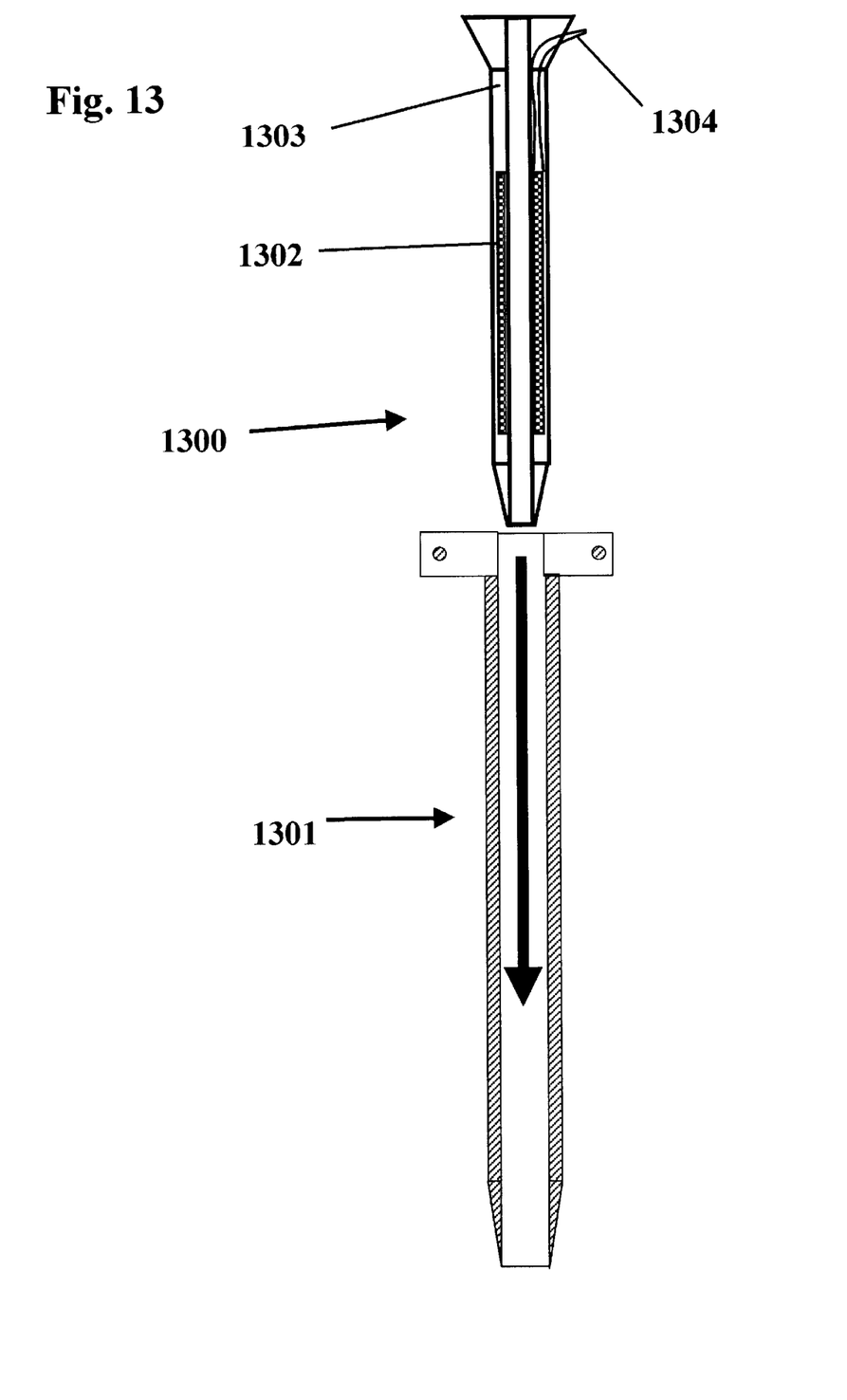
FIG. 13 is a schematic, sectional illustration of an ultrasonic generator used to apply ultrasonic energy to and invasive medical device, in accordance with a preferred embodiment of the present invention.

FIG. 13 is a schematic, sectional illustration of yet another ultrasonic generator 1300, which is used to apply ultrasonic energy to an invasive element 1301, in accordance with a preferred embodiment of the present invention. Element 1301 typically comprises a standard vascular catheter, but the principles of this embodiment may similarly be applied to other types of invasive devices. Ultrasonic generator 1300 comprises a body 1303 having a generally cylindrical, elongate shape, in which a transducer 1302 is embedded. The transducer is driven by a suitable ICM and power source (not shown) via wires 1304. As shown in the figure, generator 1300 is inserted into a lumen of invasive element 1301 as needed in order to apply ultrasonic energy to the invasive element.

It will be appreciated that the preferred embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

What is claimed is:

1. A method for reducing morbidity associated with an elongate medical device inserted into the body of a patient, comprising:

coupling an ultrasonic transducer to a portion of the elongate device that is outside the body, said portion having a longitudinal axis so that the transducer is approximately parallel to said longitudinal axis of the device; and applying ultrasonic energy to the device by actuating the transducer so as to impart vibration to the device with sufficient intensity to inhibit accretion of biological matter associated with the device while the device is in the body.

2. A method according to claim 1, wherein applying the ultrasonic energy comprises applying energy to the device so as to inhibit bacterial growth on the device.

3. A method according to claim 1, wherein applying the ultrasonic energy comprises applying energy to inhibit formation of a clot on the device.

4. A method according to claim 1, and comprising administering a therapeutic agent in conjunction with applying the ultrasonic energy.

5. A method according to claim 4, wherein the therapeutic agent comprises an antibacterial agent.

6. A method according to claim 4, wherein the therapeutic agent comprises an anti-coagulant or fibrinolytic agent.

7. A method according to claim 4, wherein administering the therapeutic agent comprises coating at least a portion of the device with the therapeutic agent.

8. A method according to claim 4, wherein administering the therapeutic agent comprises administering the agent systemically.

9. A method according to claim 1, wherein the transducer comprises a bending-type transducer.

10. A method according to claim 1, wherein the transducer comprises a transverse-type transducer.

11. A method according to claim 1, wherein actuating the transducer comprises vibrating the device in a direction perpendicular to the axis.

12. Apparatus for reducing morbidity associated with an elongate device inserted into the body of a patient, comprising an ultrasonic transducer, which is adapted to be coupled to a portion of the elongate device that is outside the body said portion having a longitudinal axis so that the transducer is approximately parallel to said longitudinal axis of the device, so as to apply ultrasonic vibration to the device with sufficient intensity to inhibit accretion of biological matter associated with the device while the device is in the body.

13. Apparatus according to claim 12, wherein the ultrasonic energy inhibits bacterial growth on the device.

14. Apparatus according to claim 12, wherein the ultrasonic energy inhibits formation of a clot on the device.

15. Apparatus according to claim 12, wherein the ultrasonic energy is applied in conjunction with administration of a therapeutic agent.

16. Apparatus according to claim 12, and comprising an integrated circuit module, which drives the transducer so as to control one or more parameters of the energy applied to the device.

17. Apparatus according to claim 16, wherein the integrated circuit module generates an oscillating electrical current to drive the transducer, and wherein the module adjusts a frequency of the oscillating current so as to match a resonant frequency of the transducer.

18. Apparatus according to claim 16, wherein the integrated circuit module is coupled to the transducer by a connector, so that a first portion of the apparatus containing the transducer may be separated after use from a second portion including the integrated circuit module.

19. Apparatus according to claim 18, wherein the first portion of the apparatus is disposed of after use, while the second portion is reused.

20. Apparatus according to claim 12, wherein the transducer comprises a bendingtype transducer.

21. Apparatus according to claim 12, wherein the transducer comprises a transverse-type transducer.

22. Apparatus according to claim 12, wherein the transducer is coupled to the device so as to cause vibration of the device in a direction perpendicular to the axis.

23. An ultrasonic energy generator for use with an elongate invasive medical device, comprising:

a ultrasonic energy generator, adapted to be mechanically coupled to a proximal portion of the invasive device that is outside the body said portion having a longitudinal axis; and a transducer, held approximately parallel to a longitudinal axis of the device by the generator body so as to apply ultrasonic vibration to the invasive device while a distal portion of the device is in the body.

24. A generator according to claim 23, wherein application of the ultrasonic energy inhibits accretion of biological matter associated with the device.

25. A generator according to claim 23, wherein the generator body comprises a fastener, which is adapted to fix the transducer to the invasive device.

26. A generator according to claim 23, wherein the transducer comprises a bending-type transducer.

27. A generator according to claim 23, wherein the transducer comprises a transverse-type transducer.

28. A generator according to claim 23, wherein the transducer is coupled to the device so as to cause vibration of the device in a direction perpendicular to the axis.

29. A medical device, comprising:

an elongate intrabody member having a longitudinal axis, for insertion into the body of a patient; and an ultrasonic transducer, which is coupled to the intrabody member so that the transducer is approximately parallel to the longitudinal axis, so as to apply ultrasonic vibration to the intrabody member with sufficient intensity to inhibit accretion of biological matter associated with the device while the device is in the body.

30. A device according to claim 29, wherein the intrabody member comprises a catheter.

31. A device according to claim 29, wherein the transducer comprises a bendingtype transducer.

32. A device according to claim 29, wherein the transducer comprises a transverse-type transducer.

33. A device according to claim 29, wherein the transducer is coupled to cause vibration of the intrabody member in a direction perpendicular to the axis.

* * * * *